United States Patent
Nichols

[11] Patent Number: 6,090,111
[45] Date of Patent: Jul. 18, 2000

[54] DEVICE FOR SECURING SPINAL RODS

[75] Inventor: David Nichols, Trumbull, Conn.

[73] Assignee: Surgical Dynamics, Inc., Norwalk, Conn.

[21] Appl. No.: 09/098,927

[22] Filed: Jun. 17, 1998

[51] Int. Cl.[7] ................................................ A61B 17/56
[52] U.S. Cl. ............................................. 606/61; 606/73
[58] Field of Search ............................. 606/61, 60, 72, 606/73; 623/17

[56] References Cited

U.S. PATENT DOCUMENTS

| | | |
|---|---|---|
| 4,269,178 | 5/1981 | Keene . |
| 4,641,636 | 2/1987 | Cotrel . |
| 4,815,453 | 3/1989 | Cotrel . |
| 4,887,596 | 12/1989 | Sherman . |
| 4,946,458 | 8/1990 | Harms et al. . |
| 5,010,879 | 4/1991 | Moriya et al. . |
| 5,074,864 | 12/1991 | Cozad et al. . |
| 5,112,332 | 5/1992 | Cozad et al. . |
| 5,116,334 | 5/1992 | Cozad et al. . |
| 5,176,678 | 1/1993 | Tsou . |
| 5,176,680 | 1/1993 | Vignaud et al. . |
| 5,181,917 | 1/1993 | Rogozinski . |
| 5,190,543 | 3/1993 | Schlapfer . |
| 5,207,678 | 5/1993 | Harms et al. . |
| 5,217,497 | 6/1993 | Mehdian . |
| 5,261,912 | 11/1993 | Frigg . |
| 5,281,222 | 1/1994 | Allard et al. . |
| 5,346,493 | 9/1994 | Stahurski et al. . |
| 5,360,431 | 11/1994 | Puno et al. . |
| 5,368,594 | 11/1994 | Martin et al. . |
| 5,443,467 | 8/1995 | Biederman et al. . |
| 5,466,237 | 11/1995 | Byrd, III et al. .................. 606/61 |
| 5,474,555 | 12/1995 | Puno et al. . |
| 5,476,462 | 12/1995 | Allard et al. . |
| 5,496,321 | 3/1996 | Puno et al. . |
| 5,507,746 | 4/1996 | Lin . |
| 5,520,690 | 5/1996 | Errico et al. . |
| 5,549,608 | 8/1996 | Errico et al. . |
| 5,554,157 | 9/1996 | Errico et al. . |
| 5,562,663 | 10/1996 | Wisnewski et al. .................. 606/61 |
| 5,615,965 | 4/1997 | Saurat et al. . |
| 5,624,440 | 4/1997 | Huebner . |
| 5,628,740 | 5/1997 | Mullane . |
| 5,630,817 | 5/1997 | Rokegem et al. . |
| 5,647,873 | 7/1997 | Errico et al. . |
| 5,669,911 | 9/1997 | Errico et al. . |
| 5,672,176 | 9/1997 | Biederman et al. . |
| 5,683,390 | 11/1997 | Metz-Stavenhagen et al. . |
| 5,683,392 | 11/1997 | Richelsoph et al. . |
| 5,690,630 | 11/1997 | Errico et al. . |
| 5,702,395 | 12/1997 | Hopf . |
| 5,797,911 | 8/1998 | Sherman et al. .................. 606/61 |

FOREIGN PATENT DOCUMENTS 0811357  8/1997  European Pat. Off. .

Primary Examiner—Michael Buiz
Assistant Examiner—Jonathan D. Goldberg

[57] ABSTRACT

A device is disclosed for securing a spinal rod to the spine comprising a fastener having a curvate head portion, a securement body having an interior cavity including a first portion having a first axis and configured to accommodate the curvate head portion of the fastener and a second portion having a second axis and configured to accommodate a spinal rod in such a manner so that the spinal rod and the curvate head portion are in contact with one another, and a locking member configured to linearly engage the second portion of the interior cavity of the securement body along the axis thereof in such a manner so as to secure the relative position of the spinal rod and the head portion of the fastener.

29 Claims, 3 Drawing Sheets

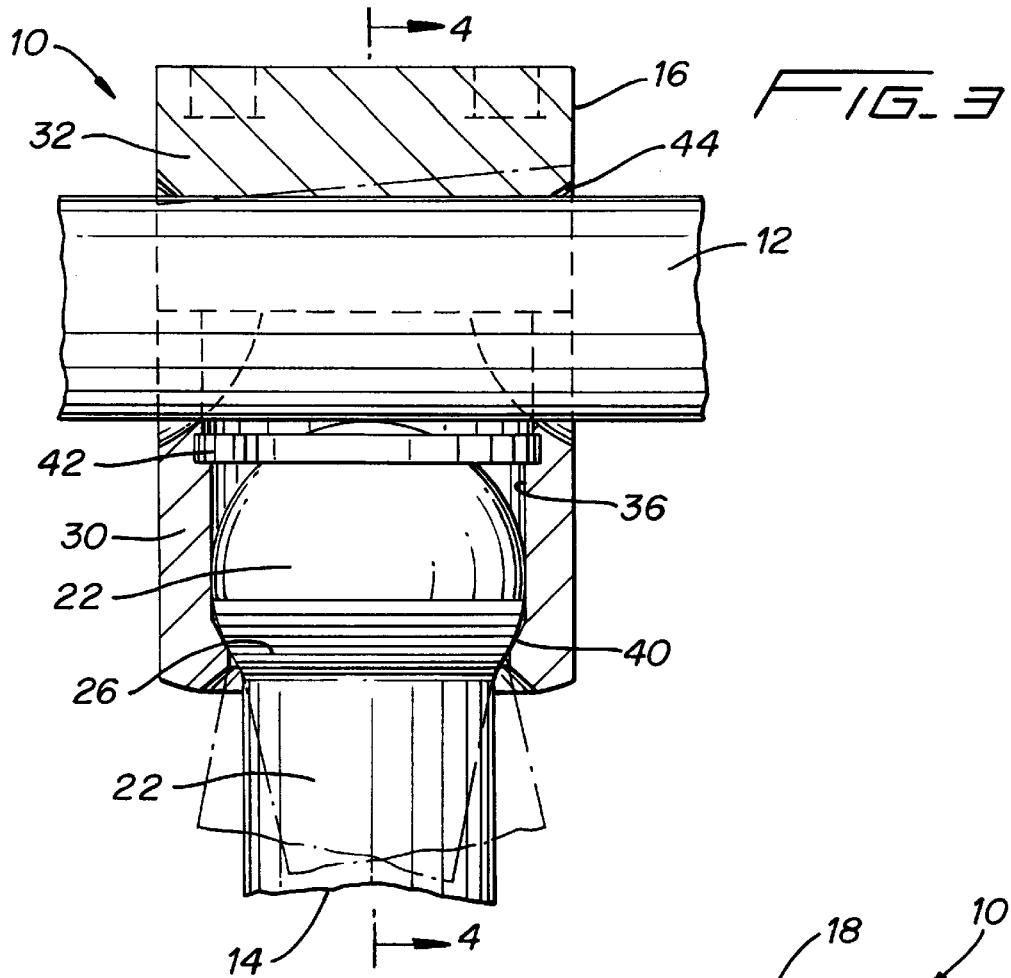
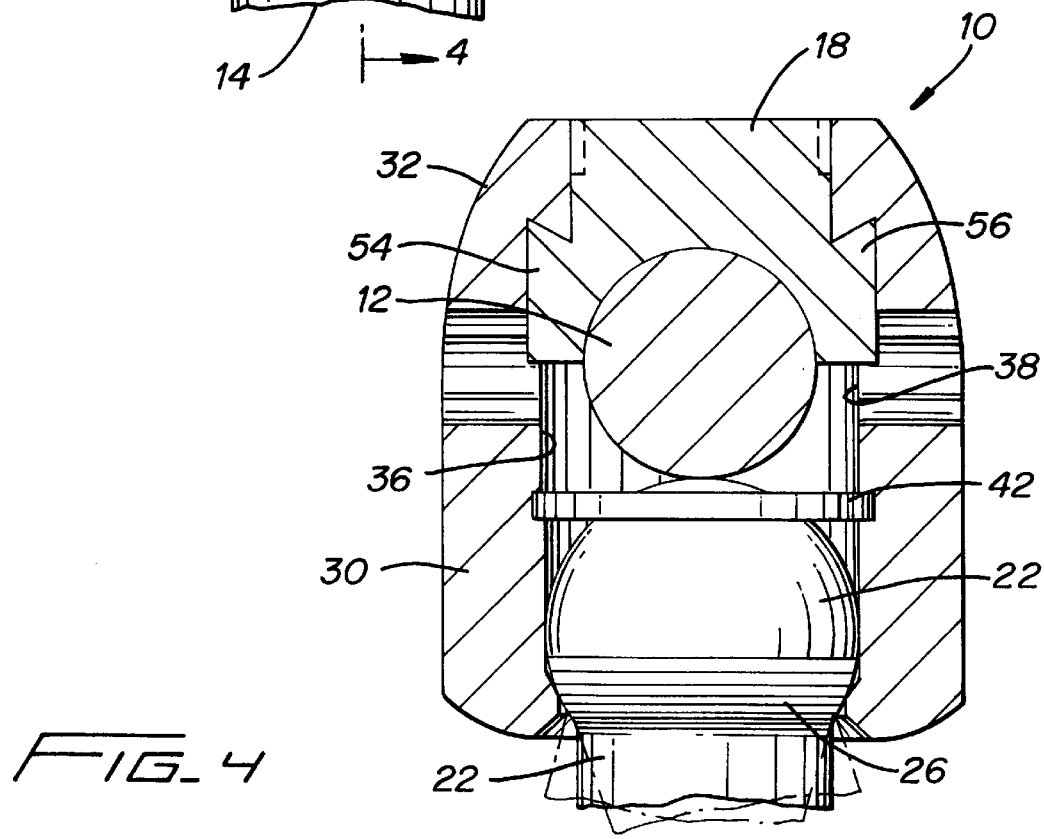

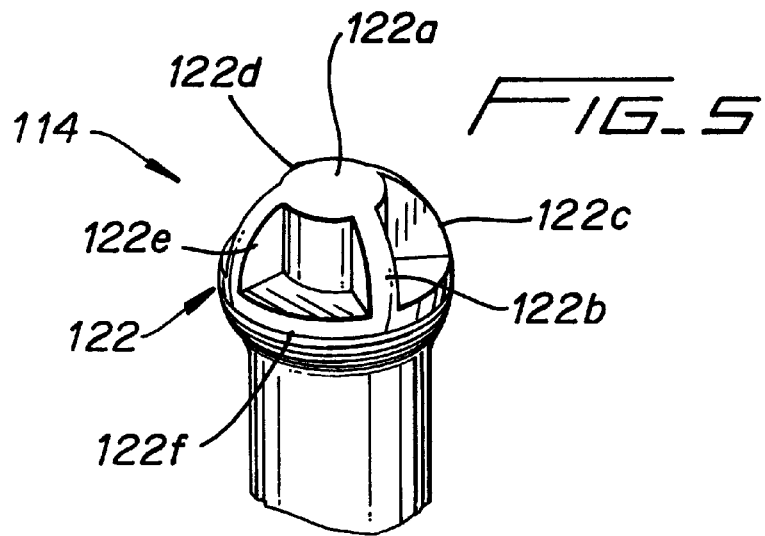
FIG_5
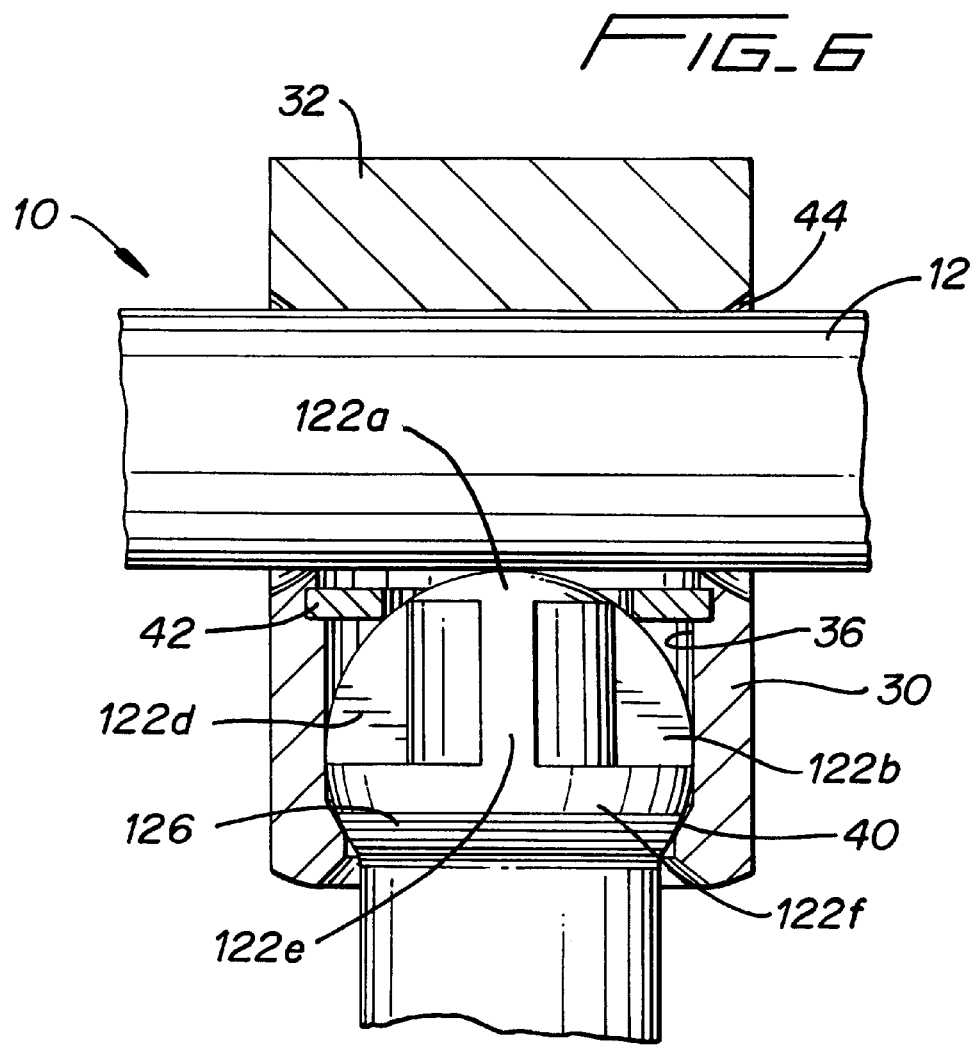
FIG_6

DEVICE FOR SECURING SPINAL RODS

BACKGROUND OF THE INVENTION

1. Field of the Invention

The subject disclosure relates to implantable spinal stabilization systems for surgical treatment of spinal disorders, and more particularly, to a device for securing a cylindrical spinal rod of a spinal stabilization system to the spine.

2. Background of the Related Art

The spinal column is a complex system of bones and connective tissue which protects critical elements of the nervous system. Despite these complexities, the spine is a highly flexible structure, capable of a high degree of curvature and twist through a wide range of motion. Trauma or developmental irregularities can result in spinal pathologies which limit this range of motion.

For many years, orthopedic surgeons have attempted to correct spinal irregularities and restore stability to traumatized areas of the spine through immobilization. Over the past ten years, spinal implant systems have been developed to achieve immobilization. Examples such systems are disclosed in U.S. Pat. Nos. 5,102,412 and 5,181,917. Such systems often include spinal instrumentation having connective structures such as elongated rods which are placed on opposite sides of the portion of the spinal column intended to be immobilized. Screws and hooks are commonly utilized to facilitate segmental attachment of such connective structures to the posterior surfaces of the spinal laminae, through the pedicles, and into the vertebral bodies. These components provide the necessary stability both in tension and compression.

It has been recognized that considerable difficulty is associated with inserting screws along a misaligned spinal curvature and simultaneously positioning coupling elements in alignment with a cylindrical spinal rod having a fixed axis without distorting the screws. Many attempts have been made in the prior art to provide instrumentation which permit angulation of a screw relative to the coupling elements of a spinal rod. Examples of such devices are disclosed in U.S. Pat. Nos. 5,549,608, 5,554,157 and 5,690,630. However, these prior art devices are connected to the spinal rod by threaded components that necessarily require the application of undesirable torsional forces to the spine. Furthermore, these threaded components can loosen under cyclically applied loads commonly encountered in the spinal column. Clearly, it would be beneficial to provide an improved device for securing spinal rods to the spinous process which provides a wide range of angular adjustability, uniform securement and which does not require the application of undesirable torsional forces during application.

SUMMARY OF THE DISCLOSURE

The subject disclosure is directed to a device for securing a spinal rod to the spine during a spinal stabilization procedure. The device includes a fastener having a head portion and body portion which depends from the head portion and has a longitudinal axis which extends therethrough. The device further includes a securement body having an interior cavity which includes a lower portion having a first axis and is configured for accommodating pivotal movement of the head portion of the fastener in such a manner so as to permit selective orientation of the longitudinal axis of the body portion of the fastener relative to the first axis of the lower portion of the interior cavity. Preferably the head portion of the fastener is curvate in configuration.

The interior cavity of the securement body further includes an upper portion having a second axis which extends perpendicular to the first axis and defines an elongate channel to accommodate a spinal rod. Preferably, the cylindrical spinal rod and the curvate head portion are in contact with one another at a location on the first axis. The device further includes a locking member configured to linearly engage the upper portion of the interior cavity of the securement body along the second axis in such a manner so as to secure the relative position of the cylindrical spinal rod and the curvate head portion and thereby fix the selected orientation of the longitudinal axis of the body portion of the fastener relative to the first axis.

Preferably, the upper portion of the interior cavity includes opposed recess areas for accommodating insertion of the head portion into the interior cavity of the securement body. In addition, the lower portion of the interior cavity of the securement body preferably includes an annular retention channel for accommodating a retaining ring in a position circumscribing the curvate head portion of the threaded fastener, and a split retaining ring is provided which is dimensioned and configured for reception within the annular retention channel.

Preferably, the locking member of the rod securing device includes a lower portion having a hemi-cylindrical channel defined therein for accommodating an upper portion of the cylindrical spinal rod. In addition, the lower portion of the locking member preferably includes a pair of laterally opposed tapered wedges dimensioned and configured to lockingly engage a corresponding pair of laterally opposed tapered slots defined in the securement body within the upper portion of the interior cavity. The locking member also preferably includes an upper portion having laterally opposed pairs of spaced apart reception ports dimensioned and configured to lockingly engage laterally opposed pairs of spaced apart locking tabs projecting from the securement body within the second portion of the interior cavity thereof.

Because the tapered wedges of the locking member engage the slots of the reception channel linearly along the axis of the cylindrical spinal rod, the application of undesirable torsional forces to the spine normally generated during the process of tightening a conventional threaded component is avoided. Furthermore, while threaded components can loosen under cyclically applied loads commonly encountered in the spinal column, the locking member remains fixed under such conditions.

These and other features of the device disclosed herein and the method of installing the same will become more readily apparent from the following description of the drawings.

BRIEF DESCRIPTION OF THE DRAWINGS

So that those having ordinary skill in the art to which the disclosed device appertains will more readily understand how to construct and use the same, reference may be had to the drawings wherein:

FIG. 3 is a cross-sectional view taken along line 3—3 of FIG. 1 illustrating the interaction between a cylindrical spinal rod and the curvate head of the fastener;

FIG. 4 is a cross-sectional view taken along line 4—4 of FIG. 1 illustrating the interaction between the linear locking member and the cylindrical spinal rod; and FIG. 5 is a perspective view of the curvate head portion of another threaded fastener constructed in accordance with the subject disclosure; and FIG. 6 is a cross-sectional view similar to that of FIG. 3 illustrating the interaction between the cylindrical spinal rod and the head portion of the fastener illustrated in FIG. 5.

Figures 1, 2:
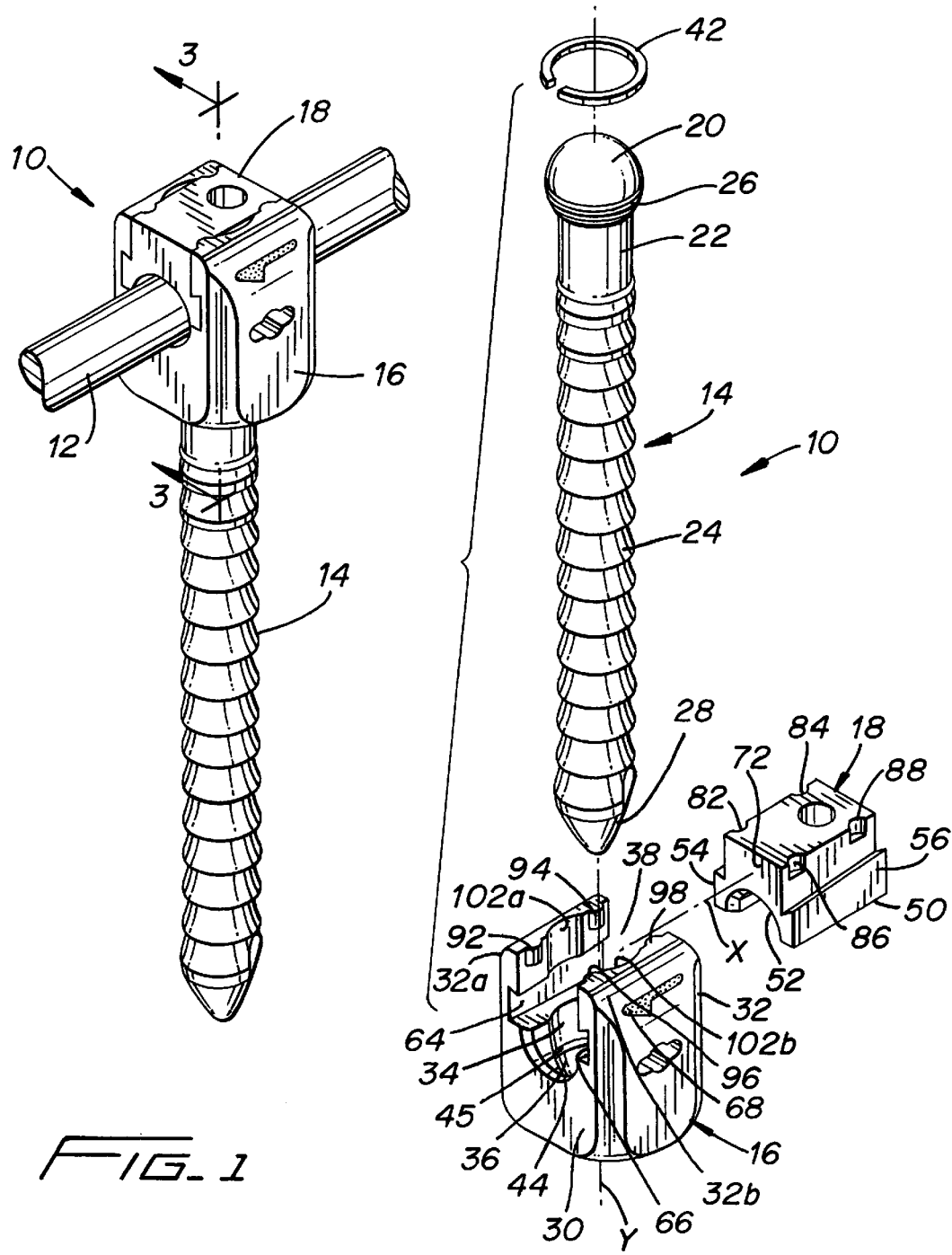
FIG. 1 is a perspective view of a device for securing a cylindrical spinal rod to the spinous process constructed in accordance with a preferred embodiment of the subject disclosure.
FIG. 2 is an exploded perspective view of the device illustrated in FIG. 1 with each of the components parts thereof separated for ease of illustration.

These and other features of the rod securement device disclosed herein will become more readily apparent to those having ordinary skill in the art from the following detailed description of the invention taken in conjunction with the drawings.

DETAILED DESCRIPTION OF THE PREFERRED EMBODIMENTS

Referring now to the drawings wherein like reference numerals identify similar structural elements of the disclosed device, there is illustrated in FIG. 1 a rod securement device constructed in accordance with a preferred embodiment of the subject disclosure and designated generally by reference numeral 10. As illustrated in FIG. 1, securement device 10 is employed in conjunction with an elongated cylindrical spinal rod 12 and is configured to secure longitudinal spinal rod 12 to the spine during a spinal stabilization procedure.

Referring now to FIGS. 1 and 2, rod securement device 10 includes a fastener 14, a securement body 16 and a locking member 18. Fastener 14 includes a curvate head portion 20, a generally cylindrical neck portion 22 which depends from the curvate head portion 20, and an elongated threaded body portion 24 which depends from the cylindrical neck portion 22. The outer surface of the curvate head portion 20 is continuous and preferably includes a series of circular ridges 26 extending about the lower hemisphere thereof, adjacent the annular neck portion 22. The threads of body portion 24 are particularly adapted to securely engage bone and define a continuous helix extending about the longitudinal axis of body portion 24 from the pointed tip 28 of fastener 14 to the neck portion 22 thereof.

With continuing reference to FIG. 2, securement body 16 includes a lower body portion 30, an upper body portion 32 and an interior cavity 34. The interior cavity 34 of securement body 16 includes a lower cavity portion 36 defined within the lower body portion 30 of securement body 16 and an upper cavity portion 38 defined within the upper body portion 32 of securement body 16. The upper cavity portion 38 of interior cavity 34 has a first longitudinal axis designated "X" extending therethrough and the lower cavity portion 36 of interior cavity 34 has a second longitudinal axis designated "Y" extending therethrough which is perpendicular to the longitudinal axis of the upper cavity portion 38.

As best seen in FIGS. 3 and 4, the lower cavity portion 36 of interior cavity 34 forms a seat for accommodating the curvate head portion 20 of fastener 14. More particularly, the lower cavity portion 36 of the interior cavity 34 of securement body 16 includes a curved surface area 40 configured for registration with the lower hemisphere of the curvate head portion 20, i.e., the section of curvate head portion 20 bearing circular ridges 26. Those skilled in the art will readily appreciate that the circular ridges provide an enhanced gripping area for the head portion 20. The curved surface area 40 of interior cavity 34 is designed to permit the selective orientation of the longitudinal axis of the threaded body portion 24 of fastener 14 relative to the longitudinal axis "Y" of the lower cavity portion 36 of interior cavity 34, as will be described in greater detail hereinbelow.

Referring back to FIG. 2, an annular channel 45 is formed in the lower body portion 30 of securement body 16 within the lower cavity portion 36 of the interior cavity 34 above the curved surface area 40 thereof. Annular channel 45 is configured to accommodate a split retaining ring 42 which is dimensioned to circumscribe the upper hemisphere of the curvate head portion 20 of fastener 14 (see FIGS. 3 and 4). When the lower hemisphere of the curvate head portion 20 of fastener 14 is in registration with the curved surface area 40 of interior cavity 34, retaining ring 42 positively retains the fastener 14 therein.

The upper cavity portion 38 of interior cavity 34 is defined in part by a hemi-cylindrical passageway 44 which intersects a region of the lower cavity portion 36 of interior cavity 34 above annular channel 45. Passageway 44 is configured to accommodate the lower hemi-cylindrical portion of spinal rod 12 and is dimensioned such that when spinal rod 12 extends through securement body 16, spinal rod 12 and curvate head portion 20 are in abutting contact at a location lying on the longitudinal axis of the lower cavity portion 36 of interior cavity 34, as illustrated in FIGS. 3 and 4. Moreover, at such a time a horizontal plane which extends tangent to the upper surface of the curvate head portion 22 is coplanar with a horizontal plane which extends tangent to the lower surface of the spinal rod 12.

Securement device 10 further includes a locking member 18 dimensioned and configured to linearly engage the upper cavity portion 38 of interior cavity 34 along the longitudinal axis "X" of the upper cavity portion 38 to positively secure the axial position of the securement body 16 with respect to spinal rod 12. Furthermore, when locking member 18 is linearly engaged in the upper cavity portion 38 of interior cavity 34, spinal rod 12 is urged against the curvate head portion 20 of fastener 14 in such a manner so as to fix the selected orientation of the longitudinal axis of the threaded body portion 24 of fastener 14. More particularly, locking member 18 includes a lower body portion 50 having a hemi-cylindrical channel 52 extending therethrough for accommodating the upper hemi-cylindrical portion of spinal rod 12 extending through the upper cavity portion 38 of interior cavity 34.

In addition, locking member 18 includes a locking mechanism in the form of a pair of laterally opposed tapered wedges 54 and 56 depending from either side of the lower body portion 50 of locking member 18 for engaging a corresponding pair of laterally opposed tapered slots 64 and 66 formed in the upper body portion 32 of securement body 16 within the upper cavity portion 38 of interior cavity 34. The tapered wedges 54, 56 and corresponding tapered slots 64, 66 employ inwardly angled sloping locking surfaces to effect positive engagement therebetween. An indicator arrow designated by reference numeral 68 is provided on the exterior surface of the upper body portion 32 of securement body 16 to indicate the proper direction in which to linearly engage locking member 18 in the upper cavity portion 38.

With continuing reference to FIG. 2 in conjunction with FIGS. 3 and 4, the upper body portion 72 of locking member 18 further includes a secondary securement mechanism consisting of laterally opposed paired retention ports 82, 84 and 86, 88. Laterally opposed retention ports 82 and 86 are disposed adjacent the leading end of locking member 18 while laterally opposed retention ports 84 and 88 are disposed adjacent the trailing end of locking member 18. The paired retention ports are dimensioned and configured to receive and securely retain corresponding paired engagement tabs 92, 94 and 96, 98 which project into the upper cavity portion 38 from the upper body portion 32 of securement body 16.

As best seen in FIG. 2, the interior surfaces of the side walls 32a and 32b of upper body portion 32 include curved recess 102a and 102b, respectively, for accommodating the passage of the curvate head portion 20 of fastener 14 when the fastener is inserted into the securement body 16 to seat the curvate head portion 20 within the lower cavity portion 36 of interior cavity 34.

Referring now to FIGS. 3 and 4, during a spinal stabilization procedure, prior to engagement of the spinal rod 12 with the securement body 16 of securement device 10, the threaded fastener 14 is inserted into the interior cavity 34 of securement body 16 such that the curvate head portion 22 passes through curved recesses 102a and 102b and registers with curved surface area 40 defined within the lower cavity portion 36 of interior cavity 34. Thereupon, the split retaining ring 42 is inserted into the annular channel 45 formed within the lower cavity portion 36 to positively retain threaded fastener 14 therein.

At such a time, the curvate head portion 22 of threaded fastener 14 is free to pivot within its seat in the lower cavity portion 36 about the longitudinal axis "Y" which extends therethrough. Consequently, the threaded body portion 24 of threaded fastener 14 may be selectively oriented at a desirable angle with respect to the longitudinal axis of the spinal rod 12 with which it is to become associated. Once the desired orientation of the threaded fastener 14 has been established, it is secured in place using conventional surgical instrumentation. At such a time, the securement body 16 is pivoted relative to the curvate head portion 22 of threaded fastener 14 so that the cylindrical rod 12 is received within passageway 44. Thereupon, the cylindrical spinal rod 12 and the curvate head portion 22 of threaded fastener 14 are in abutting contact at a location lying on the longitudinal axis of the lower cavity portion 36 of interior cavity 34.

Then, locking member 18 is linearly inserted into the upper cavity portion 38 of interior cavity 34 in the direction shown by indicator arrow 68 such that laterally opposed tapered wedges 54 and 56 depending from either side of the lower body portion 50 of locking member 18 engage the laterally opposed tapered slots 64 and 66 formed in the upper body portion 32 of securement body 16. Provisional locking of the locking member 18 within the upper cavity portion further 38 is provided by the engagement of the laterally opposed paired retention ports 82, 84 and 86, 88 formed in the upper body portion 72 of locking member 18 with the corresponding paired engagement tabs 92, 94 and 96, 98 which project into the upper cavity portion 38 from the interior surfaces of the side walls 32a and 32b of securement body 16. This provisional locking maintains the locking member 18 in place until it is finally locked upon engagement of the tapered wedges 54, 56 and tapered slots 64, 66.

Once the locking member 18 has been fully engaged in upper cavity portion 38, the geometric configuration and dimensional characteristics thereof function to urge the cylindrical spinal rod 12 into close approximation with the curvate head portion 22 of threaded fastener 14. In essence, linear engagement of the locking member 18 along the longitudinal axis of cylindrical spinal rod 12 compresses the entire mechanical construct so that the relative position of the longitudinal spinal rod 12 and the curvate head portion 22 becomes fixed, as does the relative position of the curvate head portion 22 and the curved surface 40 of lower cavity portion 36.

Referring now to FIGS. 5 and 6, there is illustrated another threaded fastener constructed in accordance with the subject disclosure and designated generally by reference numeral 114. Threaded fastener 114 includes a curvate head portion 122 which has a discontinuous curvate surface. More particularly, the curvate head portion 122 of threaded fastener 114 is defined by a curvate upper polar region 122a, four circumferentially spaced apart longitudinal arc portions 122b through 122e, and a curvate lower polar region 122f which includes a series of circular ridges 126 for interacting with the curved seating surface 40 defining the lower cavity portion 36 of securement body 16. The construction of the curvate head portion 122 of threaded fastener 114 facilitates placement as the tool can more easily grip the head of the shaft for driving or adjusting the fastener. As best seen in FIG. 6, in operation, the cylindrical spinal rod 16 is in abutting contact with the curvate upper polar region 122a of the curvate head portion 122 of threaded fastener 114. Although the device disclosed herein has been described with respect to preferred embodiments, it is apparent that modifications and changes can be made thereto without departing from the spirit and scope of the invention as defined by the claims.

What is claimed is:

1. A device for securing a spinal rod to the spine comprising:
  a) a fastener having a head portion and a body portion;
  b) a securement body having an interior cavity including a first portion and a second portion, the first portion having an opening to receive the body portion of the fastener, a first axis extending through the opening, and a configuration to accommodate the head portion of the fastener in such a manner so as to permit the pivotal movement thereof relative to the first axis, the second portion having a second axis extending perpendicular to the first axis and a configuration to accommodate a spinal rod; and
  c) a locking member configured to linearly engage the second portion of the interior cavity of the securement body in a direction extending along the second axis in such a manner so as to secure the relative position of the spinal rod and the head portion of the fastener.

2. A device as recited in claim 1, wherein the head portion is curvate in configuration.

3. A device as recited in claim 2, wherein the curvate head portion of the fastener defines a continuous curvate surface.

4. A device as recited in claim 2, wherein the curvate head portion of the fastener defines a discontinuous curvate surface.

5. A device as recited in claim 2, wherein the first portion of the interior cavity includes a curvate seat configured to register with the curvate head portion of the fastener.

6. A device as recited in claim 1, wherein the spinal rod and head portion are positioned in contact with one another within the interior cavity.

7. A device as recited in claim 1, wherein the head portion and the spinal rod contact at a location aligned with the first axis.

8. A device as recited in claim 1, wherein the first portion of the interior cavity of the securement body includes an annular retention channel for accommodating a retaining ring in a position circumscribing the head portion of the fastener.

9. A device as recited in claim 8, further comprising a split retaining ring dimensioned and configured for reception within the annular retention channel in the first portion of the interior cavity of the securement body.

10. A device as recited in claim 1, wherein the locking member includes a lower portion having a channel defined therein for accommodating an upper portion of the spinal rod.

11. A device as recited in claim 10, wherein the lower portion of the locking member includes a pair of laterally opposed tapered wedges dimensioned and configured to lockingly engage a corresponding pair of laterally opposed tapered slots defined in the securement body within the second portion of the interior cavity.

12. A device as recited in claim 11, wherein the locking member includes an upper portion having laterally opposed pairs of spaced apart reception ports dimensioned and configured to lockingly engage laterally opposed pairs of spaced apart locking tabs projecting from the securement body within the second portion of the interior cavity.

13. A device for securing a spinal rod to the spine comprising:
   a) a fastener having a head portion and a body portion;
   b) a securement body having an interior cavity including a first portion and a second portion, the first portion having an opening to receive the body portion of the fastener, a first axis extending through the opening, and a seat for accommodating the head portion of the fastener in such a manner so as to permit the pivotal movement thereof relative to the first axis, the second portion having a second axis extending perpendicular to the first axis and defining an elongate channel to accommodate a spinal rod; and
   c) a locking member configured to linearly engage the second portion of the interior cavity of the securement body in a direction extending along the second axis in such a manner so as to secure the relative position of the spinal rod and the head portion.

14. A device as recited in claim 13, wherein the head portion of the fastener defines a continuous curvate surface.

15. A device as recited in claim 13, wherein the head portion of the fastener defines a discontinuous curvate surface.

16. A device as recited in claim 14, wherein the head portion and the spinal rod contact one another at a location on the first axis.

17. A device as recited in claim 13, wherein the first portion of the interior cavity of the securement body includes an annular retention channel for accommodating a retaining ring in a position circumscribing the head portion of the fastener.

18. A device as recited in claim 17, further comprising a split retaining ring dimensioned and configured for reception within the annular retention channel in the first portion of the interior cavity of the securement body.

19. A device as recited in claim 13, wherein the locking member includes a lower portion having a hemi-cylindrical channel defined therein for accommodating an upper portion of the cylindrical spinal rod.

20. A device as recited in claim 19, wherein the lower portion of the locking member includes a pair of laterally opposed tapered wedges dimensioned and configured to lockingly engage a corresponding pair of laterally opposed tapered slots defined in the securement body within the second portion of the interior cavity.

21. A device as recited in claim 19, wherein the locking member includes an upper portion having laterally opposed pairs of spaced apart reception ports dimensioned and configured to lockingly engage laterally opposed pairs of spaced apart locking tabs projecting from the securement body within the second portion of the interior cavity.

22. A device for securing a cylindrical spinal rod to the spine comprising:
   a) a fastener having a curvate head portion and an elongated threaded body portion depending from the curvate head portion and having a longitudinal axis extending therethrough;
   b) a securement body having an interior cavity including a first portion having a first axis and defining a curvate seat for accommodating pivotal movement of the curvate head portion in such a manner so as to permit selective orientation of the longitudinal axis of the threaded body portion of the fastener relative to the first axis, and a second portion having a second axis extending perpendicular to the first axis and defining an elongate channel to accommodate a cylindrical spinal rod in such a manner so that the cylindrical spinal rod and the curvate head portion are in contact with one another at a location aligned with the first axis; and
   c) a locking member configured to linearly engage the second portion of the interior cavity of the securement body along the second axis in such a manner so as to secure the relative position of the cylindrical spinal rod and the curvate head portion to fix the selected orientation of the longitudinal axis of the threaded body portion of the fastener relative to the first axis.

23. A device as recited in claim 22, wherein the curvate head portion of the fastener defines a continuous curvate surface.

24. A device as recited in claim 22, wherein the curvate head portion of the fastener defines a discontinuous curvate surface.

25. A device as recited in claim 22, wherein the first portion of the interior cavity of the securement body includes an annular retention channel for accommodating a retaining ring in a position circumscribing the curvate head portion of the threaded fastener.

26. A device as recited in claim 25, further comprising a split retaining ring dimensioned and configured for reception within the annular retention channel in the first portion of the interior cavity of the securement body.

27. A device as recited in claim 22, wherein the locking member includes a lower portion having a hemi-cylindrical channel defined therein for accommodating an upper portion of the cylindrical spinal rod.

28. A device as recited in claim 27, wherein the lower portion of the locking member includes a pair of laterally opposed tapered wedges dimensioned and configured to lockingly engage a corresponding pair of laterally opposed tapered slots defined in the securement body within the second portion of the interior cavity.

29. A device as recited in claim 27, wherein the locking member includes an upper portion having laterally opposed pairs of spaced apart reception ports dimensioned and configured to lockingly engage laterally opposed pairs of spaced apart locking tabs projecting from the securement body within the second portion of the interior cavity.

* * * * *